United States Patent [19]

Lavon et al.

[11] Patent Number: 5,649,920

[45] Date of Patent: Jul. 22, 1997

[54] ABSORBENT ARTICLE WITH BOLSTERING WAIST FEATURE

[75] Inventors: Gary Dean Lavon, Middletown; Margaret Henderson Hasse, Wyoming; Gerald Alfred Young, Cincinnati; Bret Darren Seitz, West Chester, all of Ohio

[73] Assignee: The Procter & Gamble Company, Cincinnati, Ohio

[21] Appl. No.: 708,022

[22] Filed: Aug. 30, 1996

Related U.S. Application Data

[63] Continuation of Ser. No. 370,906, Jan. 10, 1995, abandoned, which is a continuation-in-part of Ser. No. 342,069, Nov. 18, 1994, which is a division of Ser. No. 989,270, Dec. 11, 1992, Pat. No. 5,387,207, which is a continuation-in-part of Ser. No. 935,938, Aug. 27, 1992, Pat. No. 5,318,554, which is a continuation of Ser. No. 743,950, Aug. 12, 1991, Pat. No. 5,147,345.

[51] Int. Cl.⁶ .............................. A61F 13/15; A61F 13/20
[52] U.S. Cl. ........................... 604/385.2; 604/368
[58] Field of Search ..................... 604/358, 368, 604/378, 385.1, 385.2, 369

[56] References Cited

U.S. PATENT DOCUMENTS

| | | |
|---|---|---|
| 4,578,071 | 3/1986 | Buell . |
| 4,997,428 | 3/1991 | Unnebur et al. ................. 604/368 |
| 5,061,259 | 10/1991 | Goldman et al. ................. 604/368 |
| 5,147,345 | 9/1992 | Young et al. . |
| 5,260,345 | 11/1993 | DesMarais et al. . |
| 5,295,986 | 3/1994 | Zehner et al. ................... 604/358 |
| 5,295,987 | 3/1994 | Widlun et al. ................ 604/385.1 |
| 5,318,554 | 6/1994 | Young et al. . |
| 5,330,457 | 7/1994 | Cohen .......................... 604/375 |
| 5,368,584 | 11/1994 | Clear et al. ................. 604/385.1 |
| 5,415,649 | 5/1995 | Watanabe .................... 604/385.2 |

FOREIGN PATENT DOCUMENTS

| | | |
|---|---|---|
| 0352207A1 | 1/1990 | European Pat. Off. . |
| 0532035 | 3/1993 | European Pat. Off. . |
| 0689815 | 1/1996 | European Pat. Off. . |
| 2589047 | 4/1987 | France . |

*Primary Examiner*—David H. Willse
*Assistant Examiner*—Ki Yong O
*Attorney, Agent, or Firm*—Edward J. Milbrada; Jeffrey V. Bamber; Steven W. Miller

[57] ABSTRACT

Absorbent articles are provided having a bolstering waist feature. In its preferred embodiment, the bolstering waist feature expands upon exposure to aqueous body liquids effectively tightening the diaper by stretching of the waist regions of the absorbent article. There is a resulting increase in the contractive forces in the band of lateral tension in the waist regions of the absorbent article with a corresponding reduction in the risk of waist leakage. The bolstering waist feature further provides a member resisting longitudinal bending in the waist regions of the absorbent article, particularly adjacent to a wearer's belly. This member can also act as a "strut" resisting the forces, such as those due to gravity, which tend to cause an absorbent article to slide downward. The absorbent article is additionally provided with an absorbent core comprising at least a redistribution component that is preferably capable of redistributing aqueous body liquids from the crotch region to the waist regions of the absorbent article. The redistribution component is in effective fluid communication with the bolstering waist feature.

30 Claims, 4 Drawing Sheets

ABSORBENT ARTICLE WITH BOLSTERING WAIST FEATURE

This is a continuation of application Ser. No. 08/370,906, now abandoned filed on Jan. 10, 1995; which is a continuation in part of application Ser. No. 08/342,069, filed on Nov. 18, 1994; which is a divisional of application Ser. No. 07/989,270 filed on Dec. 11, 1992, now U.S. Pat. No. 5,387,207; which is a continuation in part of application Ser. No. 07/935,938, filed on Aug. 27, 1992, now U.S. Pat. No. 5,318,554; which is a continuation of application Ser. No. 07/743,950, filed on Aug. 12, 1991, now U.S. Pat. No. 5,147,345.

FIELD OF THE INVENTION

The present invention relates to absorbent articles such as diapers, training pants, incontinent briefs, and the like, and more particularly, to absorbent articles having a waist feature providing dynamic fit about the wearer throughout the wear cycle of the absorbent article as well as improved containment characteristics for the absorbent article.

BACKGROUND OF THE INVENTION

Infants and other incontinent individuals wear absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art. For example, U.S. Pat. No. Re. 26,152, issued to Duncan and Baker on Jan. 31, 1967, describes a disposable diaper which has achieved wide acceptance and commercial success. U.S. Pat. No. 3,860,003, issued to Buell on Jan. 14, 1975, describes an elasticized leg cuff disposable diaper which has achieved wide acceptance and commercial success.

However, absorbent articles of the current art have a tendency to sag or gap away from and to slide/slip down on the body of the wearer during wear. Three modes of failure have been identified which contribute to this sagging, gapping, sliding, and slipping:

1) Forces exerted by the normal movement of a wearer as the wearer breathes, moves and changes position can cause the waist region of a diaper to rollover during normal use resulting in a reduced gasketing effect at the waist.

2) Normal wearer movement can cause the band of lateral tension created by the absorbent article's fastening system to ride down below the belly to the belly crease of the wearer. This is because of the fact that, for an irregularly shaped volume, a band of tension will seek the cross-section having the minimum circumference for that volume. Typically, absorbent articles are fastened about the waist of a wearer at or near the wearer's navel, while the minimum circumference around a wearer goes through a point slightly below the wearer's belly, at the belly crease, and through a point at the small of the back. As a result, the band of tension will tend to move toward this line of minimum circumference. The downward force generated when the absorbent article is loaded with bodily exudates also contributes to this slipping/sliding.

3) Deformation of the materials of the absorbent article itself. For example, elastic elements in a diaper are subject to a property, known as stress relaxation, that is inherent in polymeric systems, such as are used as the elastic member in elastic elements of the diaper art for providing a band of tension about a wearer's waist. That is, the contractive force exerted by an elastic member decreases with time resulting in a lessening of the force exerted by the band of tension about a wearer's waist and, further, contributes to the aforementioned sagging, gapping, or slipping. Further discussion of stress relaxation can be found in many texts on polymer science, for example: Billmeyer Jr., F. W., *Textbook of Polymer Science*, John Wiley & Sons, pp 188–190.

The net effect of this sagging, gapping, sliding, and slipping can be premature leakage and poor fit of the absorbent article about the wearer particularly in the waist regions of the absorbent article.

In order to address premature leakage in the waist regions of absorbent articles, certain commercially available absorbent articles have been provided with elastic waist features. Such elastic waist features cause the absorbent article to fit more snugly about the waist of the wearer. An example of a disposable diaper with an elastic waist feature o which has achieved wide acceptance and commercial success is disclosed in U.S. Pat. No. 4,515,595, issued to Kievit et al. on May 7, 1985. Elastic waist features will typically comprise an elasticized waistband consisting of an elastic member contractibly affixed between the topsheet and the backsheet at the ends of the absorbent article. The elasticized waistband is, thus, designed to expand and contract with the wearer's motions and to maintain the fit of the absorbent article about the waist of the wearer during use (i.e., provide sustained dynamic fit).

However, it has been found that absorbent articles having such elastic waist features designed to fit at or near the navel also have a tendency to sag, gap, slide, or slip during use. Further, the aforementioned elastic waist feature has a tendency to rollover at the front of the diaper resulting in a lack of fit about the waist of the wearer. For male wearers, in particular, rollover increases the risk of waist leakage since a male urination stream is frequently directed toward the waist due to male anatomy.

Thus, it would be advantageous to provide an absorbent article having a waist feature that provides improved fit, reduced leakage, and enhanced wearer comfort. It would further be advantageous to provide an absorbent article which has reduced sagging, gapping, and rollover at the waist of the diaper as well as reduced overall sliding/slipping of the absorbent article or the absorbent core on the wearer during use.

Therefore, it is an object of the present invention to provide an absorbent article having sustained dynamic fit about the waist of the wearer during use.

It is a further object of the present invention to provide an absorbent article having a unique bolstering waist feature that provides sustained dynamic fit and improved resistance to leakage during use.

It is a still further object of the present invention to provide an absorbent article having a unique bolstering waist feature which reduces sagging, gapping, or rollover at the front of the diaper as well as overall sliding/slipping of the absorbent article or the absorbent core during use.

It is yet an additional object to provide an absorbent article having a unique bolstering waist feature which compensates for the loss of fit due to stress relaxation in the elastic components which provide tension about the waist region of a wearer.

These and other objects of the present invention will be more readily apparent when considered in reference to the following description and when taken in conjunction with the accompanying drawings.

SUMMARY OF THE INVENTION

The present invention provides absorbent articles such as disposable diapers, incontinent briefs, training pants and the like that have a unique bolstering waist feature that improves the dynamic fit of the absorbent article and reduces the risk of premature waist leakage.

A preferred absorbent article of the present invention comprises a containment assembly preferably comprising a liquid pervious topsheet, a liquid impervious backsheet, an absorbent core positioned between the topsheet and the backsheet, a bolstering waist feature positioned longitudinally between a first transverse end of the absorbent core and a first transverse end of the absorbent article, and a fastening system for creating/maintaining lateral tension through at least a portion of the circumference of the absorbent article. In its most preferred embodiment, the bolstering waist feature is unitary with the absorbent core and the absorbent article of the present invention is further provided with pairs of side flaps which extend laterally from the longitudinal edges of the containment assembly in both waist regions thereof. Preferably, the side flaps provided in the second waist region are elasticized.

The bolstering waist feature provides a member which resists longitudinal bending in the waist region of the absorbent article of the present invention. By resisting bending, the bolstering waist feature reduces the risk of waist leakage due to rollover and sagging/gapping, particularly in the waist region.

The bolstering waist feature further co-operates with the core to resist loss of fit due to the waist of the absorbent article riding down. The bolstering waist feature and the absorbent core co-operate to form a "strut" which resists those forces such as body movement and loading with bodily exudates which tend to cause the waist of the absorbent article to ride down.

The bolstering waist feature still further compensates for loss of contractive force over time in the band of tension, which exists in the waist regions of the absorbent article, due to stress relaxation of polymeric components, in particular elastic members which provide the tension. This loss of contractive force can cause slippage with an increased risk of premature leakage. The bolstering waist feature of the present invention is able to compensate for this loss of contractive force because its thickness increases (i.e. caliper increases) as it becomes saturated with aqueous body liquids. This thickening results in an increase in the circumference of that portion of the absorbent article around which the band of tension acts and, therefore, an increase in elongation of the elastic member resulting in an increase in the contractive force provided by the elastic member.

The absorbent core of the present invention can further comprise, at least, a redistribution component that is able to redistribute aqueous body liquids from the crotch region of the absorbent article (adjacent to the fluid discharge region of a wearer) to at least one of the first or second waist regions of the absorbent article. The absorbent core of the present invention is in effective fluid communication with the bolstering waist feature so, as aqueous body liquids are absorbed, they are redistributed to the bolstering waist feature enabling it to expand.

In an alternative embodiment of the present invention, the absorbent article is provided with joined longitudinal edges at least in the waist regions instead of a fastening system. Such an embodiment is useful as a training pant, a pull-on diaper or the like.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, training pants, diaper inserts, and the like.

In its simplest form, an absorbent article of the present invention need only include an outer cover, such as a backsheet (typically relatively liquid-impervious), an absorbent core associated with this outer cover, a bolstering waist feature in effective fluid communication with this absorbent core, and a means of creating lateral tension through at least a portion of the waist region of the absorbent article. The absorbent core is capable of transporting aqueous body liquids from the crotch region of the absorbent article to at least one of the waist regions thereof. The absorbent core and the backsheet will be associated in such a manner that the absorbent core is situated between the backsheet and the fluid discharge region of the wearer of the absorbent article. The bolstering waist feature provides resistance to longitudinal bending in the waist regions of the absorbent article providing sustained positioning and fit. Further, the bolstering waist feature is capable of increasing the lateral tension in the waist regions of the absorbent article as it becomes saturated with aqueous body liquids counteracting the loss of contractive force due to stress relaxation of elastic elements therein. As used herein a diaper component becomes "saturated" with aqueous body liquids after it has absorbed an amount of aqueous body liquid having a weight that is equal to at least 8 times the weight of the component or, if the component cannot adsorb 8 times its weight of aqueous body liquid, the component is said to be saturated if it has adsorbed at least 50% of its maximum capacity for adsorption of aqueous body liquids. The means for creating lateral tension in the waist region provides the forces that hold the absorbent article about a wearer's waist. Examples of such means include, but are not limited to, a tape system with a landing zone, the tapes in such tape systems can be either elasticized or not elasticized, a mechanical fastening system, elasticized side panels and elasticized waist features or combinations thereof.

Figure 1:
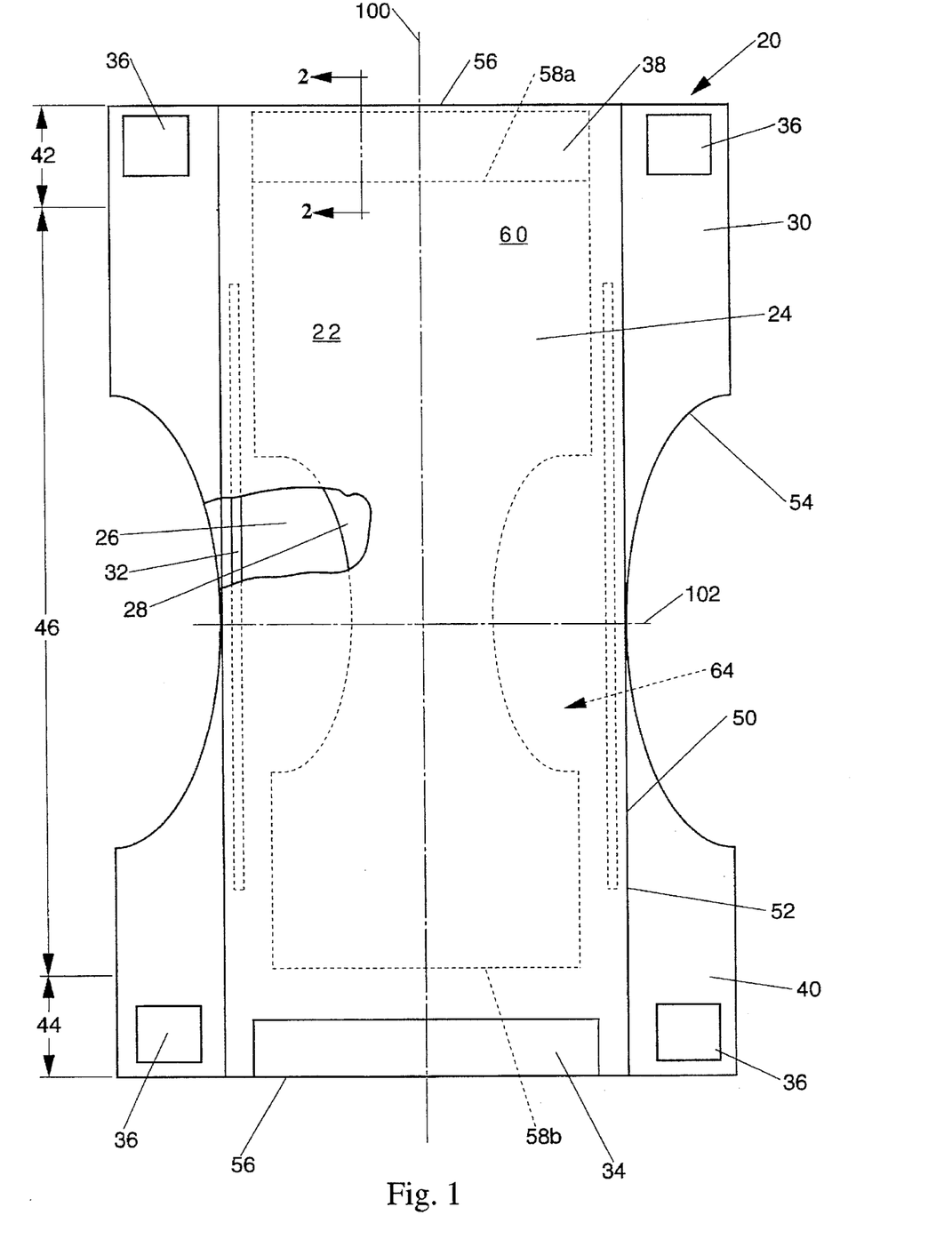
FIG. 1 is a plan view of a disposable diaper embodiment of the present invention having portions cut-away to reveal the underlying structure, and with the inner surface of the diaper facing the viewer.

FIG. 1 is a plan view of a preferred, embodiment of the present invention, the diaper 20. Diaper 20 is shown in its flat-out, uncontracted state (i.e., with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 1, the diaper 20 comprises containment assembly 22 preferably comprising a liquid pervious topsheet 24; a liquid impervious backsheet 26 joined with the topsheet 24; an absorbent core 28 positioned between the topsheet 24 and the backsheet 26; elasticized leg cuffs 32; an elastic waist feature 34; a fastening system multiply designated as 36; and a bolstering waist feature 38. The preferred embodiment diaper 20 of the present invention shown in FIG. 1 still further comprises pairs of side panels 30 and 40 joined to and extending laterally from the containment assembly 22. In the most preferred embodiment of the present invention at least a portion of side panel pair 40 is elasticized.

The diaper 20 is shown in FIG. 1 to have an outer surface 64, an inner surface 60 opposed to the outer surface 64, a first waist region 42 a second waist region 44 opposed to the first waist region 42, and a crotch region 46 positioned between the first waist region 42 and the second waist region 44, longitudinal edges 54 and end edges 56. The inner surface 60 of the diaper 20 comprises that portion of the diaper 20 which is positioned adjacent to the wearer's body during use (i.e., the inner surface 60 generally is formed by at least a portion of the topsheet 24 and other components joined to the topsheet 24). The outer surface 64 comprises that portion of the diaper 20 which is positioned away from the wearer's body (i.e., the outer surface 64 generally is formed by at least a portion of the backsheet 26 and other components joined to the backsheet 26).

The diaper 20 also has two centerlines, a longitudinal centerline 100 and a transverse centerline 102. The term "longitudinal", as used herein, refers to a line, axis, or direction in the plane of the diaper 20 that is generally aligned with (i.e. approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (i.e. divides the wearer into front and back body halves).

The containment assembly 22 is shown in FIG. 1 to have a periphery 50 which is defined by the outer edges of the containment assembly 22 in which the longitudinal edges are designated 52. The periphery 50 of the containment assembly 22 further comprises those portions of diaper end edges 56 that lie laterally between longitudinal edges 52.

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery 50 of the containment assembly 22. While the topsheet 24, the backsheet 26, and the absorbent core 28 may be assembled in a variety of well known configurations, preferred diaper configurations are described generally in U.S. Pat. No. 3,860,003 which issued to Kenneth B. Buell on Jan. 14, 1975; and U.S. Pat. No. 5,151,092, issued to Kenneth B. Buell et al. on Sep. 29, 1992; the disclosure each being incorporated herein by reference.

Figure 2:
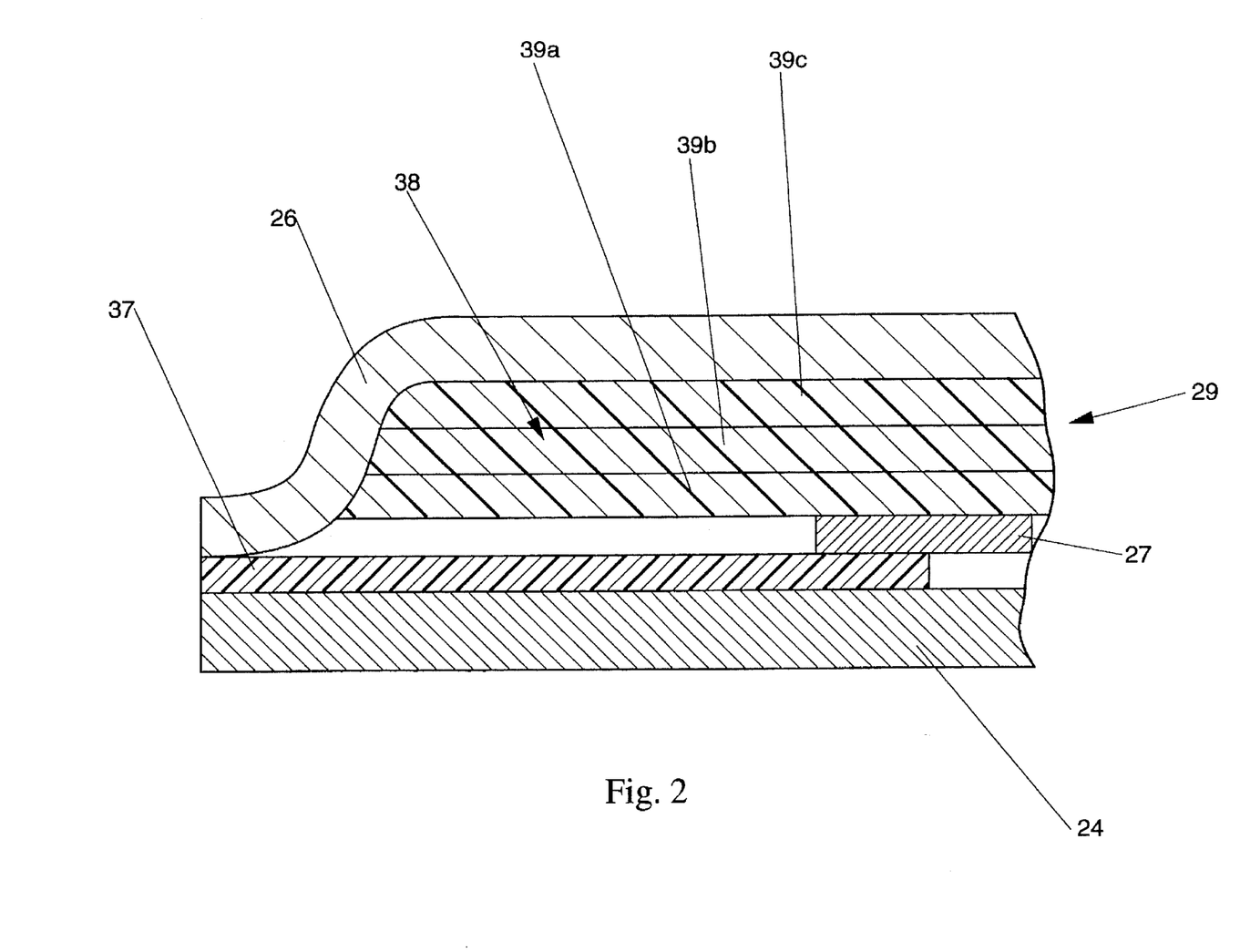
FIG. 2 is an expanded, fragmentary sectional view of the absorbent insert of FIG. 1 taken along section line 2—2 of FIG. 1.

FIG. 2 is an expanded, cross-sectional view of the diaper 20 taken along section line 2—2 of FIG. 1 showing details of the bolstering waist feature 38. As shown in FIG. 2, the preferred embodiment of the bolstering waist feature 38 is an extension of the fluid redistribution component 29 and comprises three layers of absorbent foam 39a–39c. Also shown are the components of a preferred embodiment of the absorbent core 28, the fluid acquisition component 27 and the fluid redistribution component 29. Waistshield 37, which is disposed between the bolstering waist feature 38 and the topsheet 24, is also shown.

The absorbent core 28 may comprise any absorbent means which is generally compressible, conformable, non-irritating to the wearer's skin, and capable of absorbing and retaining liquids such as urine and other certain body exudates. As shown in FIG. 1, the absorbent core 28 has a garment surface, a body surface, side edges, and first and second waist edges 58a and 58b. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; nonwoven fabrics, such as those formed using capillary channel fibers; chemically stiffened, modified or crosslinked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Also, the size and absorbent capacity of the absorbent core 28 may be varied to accommodate wearers ranging from infants through adults. Further, the first waist edge 58a of the absorbent core 28 must be in effective fluid communication with the bolstering waist feature 38 of the diaper 20. As used herein, the term effective fluid communication is intended to mean that aqueous body liquids, particularly urine, can be distributed from one component of diaper 20 to another by capillary forces, osmotic forces or other liquid transport mechanisms. The absorbent core 28 must also be capable of distributing sufficient liquid to the bolstering waist feature 38 to enable the expansion of the bolstering waist feature 38 as it is being wet with those liquids. Exemplary absorbent structures for use as the absorbent core 28 are described in U.S. Pat. No. 4,610,678, issued to Weisman et al. on Sep. 9, 1986; U.S. Pat. No. 4,673,402, issued to Weisman et al. on Jun. 16, 1987; U.S. Pat. No. 4,888,231, issued to Angstadt on Dec. 19, 1989; U.S. Pat. No. 4,834,735, issued to Alemany et al. on May 30, 1989; and U.S. Pat. No. 5,318,554, issued to Young, et al. on Jun. 7, 1994. The disclosure of each of these patents is incorporated herein by reference.

Vertical wicking, i.e., fluid wicking in a direction opposite from gravitational force, is an especially desirable performance attribute for absorbent cores described herein. This is because such absorbent cores will frequently be utilized in absorbent articles in a manner such that the aqueous body liquids to be absorbed must be moved within the article from a relatively lower position to a relatively higher position within the absorbent core of the article. For example, the diaper 20 of the present invention also comprises a bolstering waist feature 38, described in detail below, which, as it becomes saturated with aqueous body liquids, increases in volume providing increased resistance to bending in the longitudinal direction and increased lateral tension in the waist regions 42 and 44 to compensate for loss of lateral tension due to stress relaxation in elasticized elements of diaper 20. In order that the expansion aspects of the bolstering waist feature be operative over the full range of wearer motions, absorbent core 28 must be capable of redistributing aqueous body liquids that might be absorbed in crotch region 46 at least to one of first waist region 42, second waist region 44 or to both waist regions. Thus, vertical wicking enables this redistribution for instances when the waist regions 42 and 44 are relatively higher than the crotch region 46 (e.g. when the wearer is sitting or standing). Methods for measuring the vertical wicking properties of diaper core components are described in the TEST METHODS section of U.S. Pat. No. 5,387,207, issued to Dyer, et al. on Feb. 7, 1995, the disclosure of which is incorporated by reference.

As is shown in FIG. 2, a particularly preferred embodiment of absorbent core 28 comprises a fluid acquisition component 27 and a fluid redistribution component 29. The fluid acquisition component 27 can comprise any porous, hydrophilic material which will imbibe and distribute aqueous body liquids. Frequently, such absorbent materials are foam-based or fiber-based in nature. The fluid redistribution component 29 can comprise any of the materials discussed above as suitable for the absorbent core 28 as long as the fluid redistribution component 29, alone or in combination with acquisition component 27, provides the absorbent core 28 with those vertical wicking properties which allow it to enable the expansion aspects of the bolstering waist feature 38.

A preferred embodiment of the fluid redistribution component 29 comprises at least one layer of the absorbent foam material described in U.S. Pat. No. 5,268,224 issued, to DesMarais, et al. on Dec. 7, 1993, the disclosure of which is incorporated herein by reference. Absorbent foam materials of the type described therein are preferably made by polymerizing high internal phase water-in-oil emulsions (HIPE foams). They will typically have a free absorbent capacity of from about 20 to about 100 ml/g and a specific surface area per foam volume of at least about 0.025 $m^2$/cc. As used herein, the term "free absorbent capacity" refers the total amount of test fluid (Jayco synthetic urine) which a given foam sample will absorb into its cellular structure per unit mass of solid material in the sample and the term "specific surface area per foam volume" refers to the capillary suction specific surface area of the foam structure times its foam density in the expanded state. To be especially useful in absorbent articles for absorbing urine, the preferred absorbent foams of the present invention will generally also have a capillary absorption pressure of at least about 24.1 cm (9.5 inches), preferably at least about 30 cm (11.8 inches) and most preferably at least about 40 cm (15.7 inches). As used herein, the term "capillary absorption pressure" is the height at which the vertical wicking absorbent capacity is 50% of the free absorbent capacity. Methods for measuring most of these properties are described in the TEST METHODS section of U.S. Pat. No. 5,387,207, issued to Dyer, et al. on Feb. 7, 1995 the disclosure of which is incorporated by reference. The procedure for determining the free absorbent capacity of the foam is described hereafter in the TEST METHODS section.

The particularly preferred absorbent core 28 shown in FIG. 2 has a fluid redistribution component 29 comprising three layers of the HIPE foam described above. Additional details regarding absorbent cores 28 of this type are described in U.S. Pat. No. 5,318,554, issued to Young, et al., on Jun. 7, 1994, the disclosure of which is incorporated herein by reference.

These preferred absorbent foam structures will frequently be utilized in absorbent articles along with other types of absorbent structures that can also participate in acquiring, distributing and/or storing aqueous fluids. In those contexts, wherein the absorbent foam structures herein are to serve primarily as a fluid redistribution component in absorbent articles, it is desirable for such foams to have a propensity for pulling aqueous body liquids into such a redistribution component from other absorbent components, such as an acquisition component, that also have absorbed such fluids. Such a propensity to drain fluid from other absorbent article components is known in the art as "partitioning." The concept of partitioning and certain procedures for determining partitioning performance are described, for example, in the aforementioned U.S. Pat. No. 4,610,678. When tested for partitioning performance using procedures similar to those disclosed in U.S. Pat. No. 4,610,678, these preferred absorbent foam structures exhibit especially desirable fluid partitioning characteristics.

The backsheet 26 is positioned adjacent the garment surface of the absorbent core 28. The backsheet 26 prevents the exudates absorbed and contained in the absorbent core 28 from wetting articles which contact the diaper 20 such as bedsheets and undergarments.

The backsheet 26 is typically impervious to aqueous body liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 may thus comprise a woven or nonwoven material, polymeric films such as thermoplastic films of polyethylene or polypropylene, or composite materials such as a film-coated nonwoven material.

Preferably, the backsheet is a thermoplastic film having a thickness of from about 0.012 mm (0.5 mil) to about 0.051 mm (2.0 mils). Particularly preferred materials for the backsheet include RR8220 blown films and RR5475 cast films as manufactured by Tredegar Industries, Inc. of Terre Haute, Ind. The backsheet 26 is preferably embossed and/or matte finished to provide a more clothlike appearance. Further, the backsheet 26 may permit vapors to escape from the absorbent core 28 (i.e., breathable) while still preventing exudates from passing through the backsheet 26.

The topsheet 24 is positioned adjacent the body surface of the absorbent core 28 and is preferably joined to the backsheet 26 by attachment means (not shown) such as those well known in the art. For example, the topsheet 24 may be secured to the backsheet 26 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258 and by Findley Adhesives Wauwatosa, Wis. as H2031. The attachment means will preferably comprise an open pattern network of filaments of adhesive as is disclosed in U.S. Pat. No. 4,573,986, which issued to Minetola et al. on Mar. 4, 1986, the disclosure of which patent is incorporated herein by reference. Alternatively, the attachment means may comprise heat bonds, pressure bonds, ultrasonic bonds, dynamic mechanical bonds, or any other suitable attachment means or combinations of these attachment means as are known in the art. As used herein, the term "joined" encompasses configurations whereby an element is directly secured to the other element by affixing the element directly to the other element, configurations whereby the element is indirectly secured to the other element by affixing the element to intermediate member(s) which in turn are affixed to the other element, and configurations whereby the element is held in a constrained position proximate the other element without being directly or indirectly secured to the other element. In a preferred embodiment of the present invention, the topsheet 24 and the backsheet 26 are joined to each other in the periphery 50 of the containment assembly 22 by the attachment means (not shown) and the absorbent core 28 is constrained between them. That is, the absorbent core 28 is allowed to "float" between the topsheet 24 and the backsheet 26.

The topsheet 24 is compliant, soft feeling, and non-irritating to the wearer's skin. Further, the topsheet 24 is liquid pervious permitting aqueous body liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a substantially hydrophobic material to isolate the wearer's skin from liquids contained in the absorbent core 28. There are a number of manufacturing techniques which may be used to manufacture the topsheet 24. For example, the topsheet 24 may be a nonwoven web of fibers spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) Aforementioned U.S. Pat. No. 3,860,003 describes a disposable diaper which provides a contractible leg opening having a side flap and one or more elastic members to provide an elasticized leg cuff (gasketing cuff). U.S. Pat. No. 4,909,803, issued to Aziz et al. on Mar. 20, 1990, describes a disposable diaper having "stand-up" elasticized flaps (barrier cuffs) to improve the containment of the leg regions. U.S. Pat. No. 4,695,278, issued to Lawson on Sep. 22, 1987, describes a disposable diaper having dual cuffs including a gasketing cuff and a barrier cuff While each elasticized leg cuff 32 may be configured so as to be similar to any of the leg bands, side flaps, barrier cuffs, or elastic cuffs described above, it is preferred that each elasticized leg cuff 32 comprise the dual extended cuffs described in commonly assigned PCT Patent Application No. WO 94/18927, published on Sep. 1, 1994, the disclosure which is incorporated herein by reference.

The diaper 20 may further comprise an elastic waist feature 34 that provides improved fit and containment. The elastic waist feature 34 is that portion or zone of the diaper 20 which is intended to elastically expand and contract to dynamically fit the wearer's waist. In the preferred embodiment of the present invention shown in FIG. 1 the elastic waist feature 34 extends longitudinally inward from, and generally forms at least a portion of, diaper end edge 56 located in second waist region 44 toward second waist edge 58b of the absorbent core 28 located in second waist region 44. While the elastic waist feature or any of its constituent elements can comprise a separate element affixed to the diaper 20, the elastic waist feature 34 is preferably constructed as an extension of other elements of the diaper such as the backsheet 26 or the topsheet 24, preferably both the backsheet 26 and the topsheet 24.

The elastic waist feature 34 may be constructed in a number of different configurations including those described in the above referenced U.S. Pat. Nos. 4,515,595 and 5,151,092; the disclosure of each of these references is incorporated herein by reference.

The diaper 20 also comprises a fastening system 36 which forms a side closure which maintains the first waist region 42 and the second waist region 44 in an overlapping configuration such that lateral tensions are maintained around the circumference of the diaper to maintain the diaper on the wearer. Exemplary fastening systems are disclosed in U.S. Pat. No. 4,846,815, issued to Scripps on Jul. 11, 1989; U.S. Pat. No. 4,894,060, issued to Nestegard on Jan. 16, 1990; U.S. Pat. No. 4,946,527, issued to Battrell on Aug. 7, 1990; U.S. Pat. No. 3,848,594, issued to Buell on Nov. 19, 1974; and U.S. Pat. No. B1 4,662,875, issued to Hirotsu et al. on May 5, 1987; the disclosure of each being incorporated herein by reference. Any of the above-mentioned fastening systems would be suitable for diaper 20 of the present invention. The preferred embodiment of the fastening system 36 should further provide that the band of lateral tension around the circumference of the diaper should pass through the bolstering waist feature 38. Such preferred fastening systems 36 can comprise either tape or mechanical fastening means. For example, a suitable fastening system 36 could comprise a tape tab, a release portion for protecting the adhesive on the tape tab and a landing zone wherein the tape tab is located in one of the first or second waist regions 42 or 44, preferably in second waist region 44, adjacent to an end edge 56 in that waist region and the landing zone is located in the other of the waist regions 44 or 42, preferably in the first waist region 42, adjacent the end edge 56 in that waist region.

The diaper 20 shown in FIG. 1 preferably further comprises side panels 30 in first waist region 42 and side panels 40 in second waist region 44. These side panels 30 and 40 may be formed from extensions of the topsheet 24, or backsheet 26, or both. Preferably, side panels 30 and 40 comprise discrete members that are joined to and extend laterally outward from each longitudinal edge 52 of containment assembly 22 in, at least, waist regions 42 and 44 respectively. Portions of the side panels 30 and 40 can further be joined to and extend laterally outward from each longitudinal edge 52 of containment assembly 22 in the crotch region 46. The side panels 30 and 40 can be joined to the containment assembly 22 by any means familiar to the art. For example, side panels 30 and 40 may be joined to containment assembly 22 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986, which issued to Minetola et al. on Mar. 4, 1986, more preferably several lines of adhesive filaments swirled into a spiral pattern such as is illustrated by the apparatus and methods shown in U.S. Pat. No. 3,911,173, issued to Sprague, Jr. on Oct. 7, 1975; U.S. Pat. No. 4,785,996, issued to Ziecker, et al. on Nov. 22, 1978; and U.S. Pat. No. 4,842,666, issued to Werenicz on Jun. 27, 1989. The disclosure of each of these patents is incorporated herein by reference. Alternatively, the attachment means may comprise heat bonds, pressure bonds, ultrasonic bonds, dynamic mechanical bonds, or any other suitable attachment means or combinations of these attachment means as are known in the art.

Side panels 30 and 40 can be made from any materials familiar to the art. For example side panels 30 and 40 can be made from thin, flexible plastic films, porous foams, woven or nonwoven webs of natural or synthetic fibers. The side panels 30 and 40 can also be made from laminates combining such materials. A particularly preferred material for side panels 30 and 40 comprises a laminate of a nonwoven web of staple length polypropylene fibers such as is manufactured by Veratec, Inc., a division of International Paper Company, of Walpole, Mass. under the designation P-8 with a thin thermoplastic film such as RR8220 blown film and RR5475 cast film as manufactured by Tredegar industries, Inc. of Terre Haute, Ind.

In a still more preferred embodiment of the present invention side panels 30 in the first waist region 42 or, preferrably, side panels 40 in the second waist region 44 are elasticized. The elasticized panels provide an elastically extensible feature that provides a more comfortable and contouring fit by initially conformably fitting the diaper to the wearer and sustaining this fit throughout the time of wear well past the point at which the diaper has been loaded with exudates since the elasticized panels allow the sides of the diaper to expand and contract. The elasticized panels further provide more effective application of the diaper 20 since even if the diaperer pulls one elasticized panel farther than the other during application (asymmetric application), the diaper 20 will "self-adjust" during wear. While the diaper 20 of this preferred embodiment of the present invention preferably has the elasticized panels operatively associated with side panels 40 which are disposed in second waist region 44, the diaper 20, alternatively, may be provided with elasticized side panels disposed in the first waist region 42 or in both the first waist region 42 and the second waist region 44.

While the elasticized panels may be constructed in a number of configurations, examples of diapers with elasticized panels positioned in the ears (ear flaps) of the diaper are disclosed in U.S. Pat. No. 4,857,067 issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; U.S. Pat. No. 5,358,500 issued to LaVon, et al. on Oct. 25, 1994; and the hereinbefore referenced U.S. Pat. No. 5,151,092; the disclosure of each being incorporated herein by reference. For example, elasticized panels can comprise a laminate of a nonwoven web, an elastic member and a thin, flexible thermoplastic film. Suitable materials for the nonwoven web and the thin, flexible thermoplastic film have been described above with respect to the topsheet 24 and the backsheet 26 respectively. A suitable material for the elastic member is manufactured by Exxon Chemical Company, Lake Zurich, Ill., under the designation EXX 550. Such laminates can then be subjected to mechanical stretching sufficient to permanently elongate the nonwoven web and the thermoplastic film using a process such as that described in the above-mentioned U.S. Pat. No. 5,151,092 to form the elasticized panel. Alternatively, the nonelastic portions of the side panels can be gathered prior to combining them with the elastic member.

The preferred elasticized panels comprise a structural elastic-like film (SELF) web. A structural elastic-like film web is an extensible material that exhibits an elastic-like behavior in the direction of elongation without the use of added elastic materials. The SELF web includes a strainable network having at least two contiguous, distinct, and dissimilar regions. One of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in the copending, commonly assigned U.S. patent application Ser. No. 08/203, 456, filed by Donald C. Roe, et al. on Feb. 24, 1994, the disclosure of which is incorporated herein by reference.

As is also shown in FIG. 2, the diaper 20 further comprises a waistshield 37. Waistshield 37 is provided in order to prevent leakage of aqueous body liquids from the bolstering waist feature 38 (described below) through the topsheet 24. In the preferred embodiment of the present invention shown in FIGS. 1 and 2, the waistshield is secured to the topsheet 24 in the waist region 42 of diaper 20. In the more general case, a waistshield 37 would be secured to the topsheet 24 in any waist region of diaper 20 that also contains a bolstering waist feature 38. Waistshield 37 extends longitudinally outward from slightly below the waist edge 58a of the absorbent core 28 where it partially covers one transverse end of the acquisition component 27 of the absorbent core 28 to the diaper end edge 56 located in first waist region 42. Waistshields of this type are discussed in greater detail in U.S. Pat. No. 4,578,071, issued to Kenneth B. Buell on Mar. 25, 1986, the disclosure of which is incorporated herein by reference.

Waist shield 37 is impervious to aqueous body liquids. It is preferably manufactured from a thin plastic film although other flexible, liquid impervious materials may be used. The waist shield 37 may thus comprise materials with essentially the same properties as are suitable for the backsheet 26. A preferred material for the waist shield 37 is a thermoplastic film having a thickness from about 0.012 mm (0.5 mil) to about 0.051 mm (2.0 mil).

The diaper 20 still further comprises a bolstering waist feature 38. As used herein, the term bolstering waist feature means a component of diaper 20, located in first waist region 42 or in second waist region 44 or in both waist regions that resists loss of fit or premature leakage at the waist due to at least one of the failure modes described above. In the preferred embodiment of the present invention diaper 20 shown in FIGS. 1 and 2, the bolstering waist feature 38 is shown as an extension of a portion of the absorbent core 28 into the first waist region 42 of the diaper 20. Most preferably, the bolstering waist feature 38 extends longitudinally from the first waist edge 58a of the absorbent core 28 to a longitudinal position adjacent transverse end 56 in first waist region 42 of diaper 20. Alternatively, a diaper of the present invention could have a bolstering waist feature located in second waist region 44 or in both waist regions 42 and 44. At a minimum, the bolstering waist feature 38 must extend longitudinally from an end edge 58a or 58b of core 28 into first or second waist regions 42 or 44 and through the band of tension provided to the waist regions by the fastening system 36. Further, the bolstering waist feature of the present invention is contemplated to comprise extensions of the absorbent core 28 or one or more separate elements that are in effective fluid communication with absorbent core 28 or both.

As illustrated in FIG. 2, the preferred bolstering waist feature 38 comprises at least one layer of a material, preferrably an absorbent foam having the physical properties as described in the aforementioned U.S. Pat. No. 5,268,224. In the preferred embodiment shown in FIG. 2, the bolstering waist feature 38 comprises three layers of this foam 39a–39c. These layers 39a–39c are, typically, not joined together by adhesive but are simply extensions of the fluid redistribution component 29 and, therefore, are in effective fluid communication with each other and with fluid acquisition component 27.

Bolstering waist feature 38 must have physical or chemical properties that counteract at least a portion of the negative effects of the various modes responsible for loss of fit or premature leakage at the waist that is due to sagging, slippage or roll over as exhibited by diapers of the current art.

In its simplest form, for example, a diaper comprising only a topsheet 24, a backsheet 26, a core 28, elasticized leg cuffs 32, a means for creating lateral tension in the waist region, such as a fastening system 36, and a bolstering waist feature 38, the bolstering waist feature 38 would provide improved fit and containment when compared to an absorbent article having a similar construction with an elastic waistband of the current art instead of the bolstering waist feature 38.

An advantage of the absorbent articles of the present invention is that they provide resistance to loss of fit and containment due to rollover, slipping/sliding or sagging/gapping. When absorbent articles are worn, loss of stiffness in the waist area, particularly due to the repeated application of the forces encountered during normal wear, can cause the core materials to slump down, away from the waist regions of the absorbent article and into the crotch regions so the contribution of the core materials to stiffness in the waist regions is substantially eliminated. Specifically, the bolstering waist feature 38 provides an improved stiffness component, which provides a bending resistance, even after repeated applications of the forces encountered during normal wear which tend to cause rollover, slipping/sliding or sagging/gapping, counteracting those forces. Without such a stiffness component, stomach expansion can push on the top waist of an absorbent article causing it to rollover and move downward.

For example, one measure of this stiffness component is cantilever bending value. It has been found that a bolstering waist feature 38 with a dry cantilever bending value of greater than about 8.3 cm (3.3 in), preferably greater than about 9.4 cm (3.7 in) will provide a satisfactory resistive force counteracting bending when the absorbent article is dry or partially wet. Importantly, as the bolstering waist feature 38 becomes saturated with aqueous body liquids, that is, when the risk of leakage at the waist is highest, the bolstering waist feature 38 at least maintains a force resistive to rollover equal to the resistive force when the diaper 20 is dry. This resistance to rollover when wet is shown by cantilever bending values that increase to greater than about 9.9 cm (3.9 in), preferably to greater than about 10.7 cm (4.2 in), most preferably to greater than about 11.6 cm (4.6 in) when a bolstering waist feature 38 of the present invention is saturated with synthetic aqueous body liquids. A method for measuring dry and saturated cantilever bending values is provided in the Test Methods section below.

These changes in stiffness on wetting with aqueous body liquids can be clearly seen if defined in terms of a cantilever bending ratio. As used herein, the term "cantilever bending ratio" is defined as the ratio of the cantilever bending value when the absorbent article is saturated with synthetic aqueous body liquids to the cantilever bending value when the absorbent article is dry. Absorbent articles of the present invention have been found to have a cantilever bending ratio of, about 1.0:1 or greater. Absorbent articles of the present invention having this minimum cantilever bending ratio will at least maintain their dry stiffness in the waist regions when it is saturated with synthetic aqueous body liquids. Preferably, the cantilever bending ratio for an absorbent article of the present invention is greater than 1.1:1, and most preferably greater than 1.3:1. That is, preferred embodiments of an absorbent article of the present invention increase in stiffness when they are saturated with synthetic aqueous body liquids.

Further, bending resistance is maintained even when the bolstering waist feature 38 has been flexed multiple times. For example, the dry cantilever bending value after the bolstering waist feature 38 has been cyclically flexed is at least about 8.0 cm (3.5 in). Repeating this test when the bolstering waist feature 38 is saturated with synthetic aqueous body liquids results in a cantilever bending value of at least about 9.6 cm (3.8 in), preferably greater than about 11.1 cm (4.4 in). A method for determining stiffness retention on cyclical flexing is given in the TEST METHODS section below.

A stiffness retention ratio can also be defined. As used herein, the term "stiffness retention ratio" is defined as the ratio of cantilever bending values measured on the same sample before and after the sample has been cyclically flexed for 20 cycles (see TEST METHODS section). The stiffness retention ratio can be calculated for either dry samples or for samples that have been saturated with synthetic aqueous body liquids. Bolstering waist features of the present invention have a stiffness retention ratio of at least about 0.90 when dry, preferably greater than about 0.95. When the sample is saturated with synthetic aqueous body liquids the stiffness retention ratio is at least about 0.88, preferably greater than about 0.92.

Figure 3:
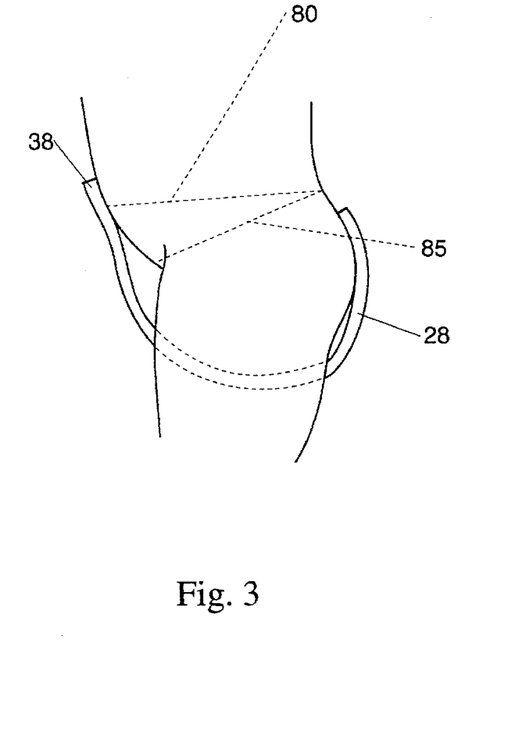
FIG. 3 is a partial side view of an infant wearing a disposable diaper embodiment of the present invention showing the preferred location of the absorbent core and the bolstering waist feature on a wearer.
Figure 4:
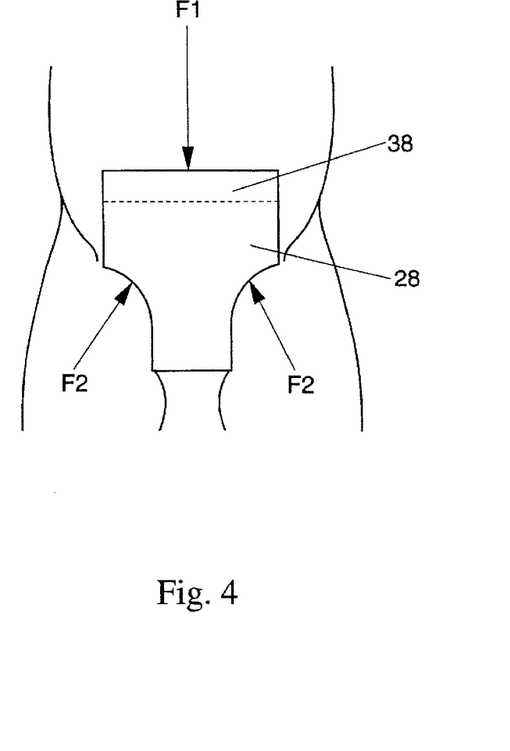
FIG. 4 is a partial frontal view of a diaper of the present invention while, it is being worn, showing how the bolstering waist feature and the core cooperate to inhibit slipping or riding down.

The bolstering waist feature 38 of the present invention and the absorbent core 28 can also co-operate to provide a resistive force that helps to prevent even the simple absorbent article with no elasticized waist features or side panels described above from riding down due to either normal body movement or the downward force created when the absorbent article is loaded with bodily exudates. This co-operation is shown in FIGS. 3 and 4 which show an infant wearer of a diaper embodiment of the present invention.

As can be seen in those figures, the minimum circumference 85 around an infant is along a line around the infant wearer which connects a point slightly below the belly, at the belly crease, and a point on the small of the back. The band of lateral tension provided, for example, by a fastening system 36, is said to ride down if the waistband of a diaper moves from where it is applied 80 (typically around the waist of a wearer at or near the wearer's navel and above the belly crease) to overlie this line of minimum circumference 85. The band of tension is predisposed to move toward the line of minimum circumference 85 because tension will be reduced as it does so.

When the bolstering waist feature 38 is an extension of or unitary with the absorbent core 28, as in the preferred embodiment of the present invention shown in FIGS. 1 and 2, the two components of the diaper co-operate to dissipate those forces $F_1$, due to normal wearer movement or to loading with bodily exudates, that would otherwise serve to cause the diaper to ride down by providing a resistive force $F_2$ at the wearer's legs. That is, the bolstering waist feature 38 and the absorbent core 28 work as a "strut" transferring such forces from the waist regions of a diaper to the wearer's legs. This cooperation is illustrated in FIG. 4. The loss of mechanical integrity when core components of absorbent articles of the current art become saturated with aqueous body liquids prevents such co-operation therein.

Further, when an absorbent article is provided with elasticized portions to help provide lateral tension in the waist regions of the diaper 20, such as the elasticized side panels 40 of the preferred embodiment of the present invention shown in FIG. 1, the bolstering waist feature 38 provides the additional benefit of compensating for stress relaxation in the polymeric systems used as elastic members in such elasticized portions. As discussed in greater detail below, the caliper of the bolstering waist feature 38 increases as it becomes saturated with aqueous body liquids. This caliper growth increases the overall absorbent article circumference at the waist and thus elongates the elasticized portions in the waist region of the absorbent article compensating for stress relaxation with the increased contractive force caused by the elongation of the elasticized portions.

Figure 5:
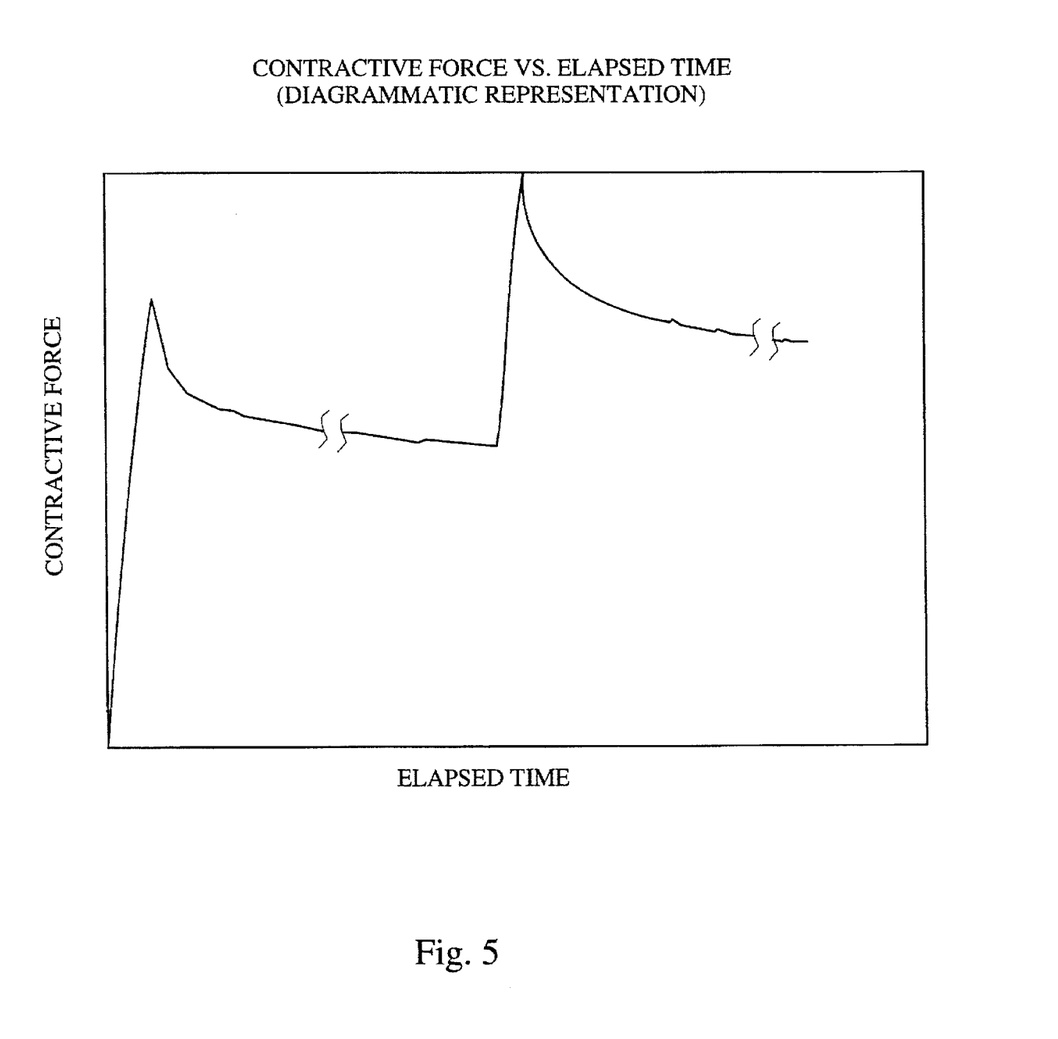
FIG. 5 is a diagrammatic representation of contractive force versus time for an elasticized feature of the present invention, showing how the bolstering waist feature of the present invention counteracts loss of contractive force due to stress relaxation.

FIG. 5 shows a diagrammatic representation of the changes in contractive force within the band of tension in the waist region of the preferred embodiment of the present invention, diaper 20. When diaper 20 is applied to a wearer, the contractive forces are determined by the amount of stretch provided to the elastic elements in the waist region during application which form the band of tension. This is shown in the first portion of FIG. 5 when the contractive force goes from essentially zero to a maximum over a very short time (i.e., during application the elastic elements are rapidly stretched to a given elongation and the elongation is then fixed by the fastening system). With time, the contractive forces in the waist decrease substantially due to stress relaxation. These reduced contractive forces can contribute to gapping in the waist region of a diaper with resulting loss of fit and increased risk of leakage at the waist because the contractive forces within the band of tension are reduced.

However, for an absorbent article of the present invention, the bolstering waist feature 38 compensates for this loss of contractive force due to stress relaxation. This compensation for loss of contractive force due to stress relaxation is shown in the second portion of FIG. 5 by the second increase in contractive force over a very short period of time. The bolstering waist feature 38 compensates for stress relaxation by effectively increasing the degree of stretch for the elastic elements within the band of tension around the circumference of the absorbent article.

The bolstering waist feature 38 compensates for stress relaxation by growing in caliper as it is exposed to aqueous body liquids. Since the only direction the bolstering waist feature can increase in caliper when it is exposed to (i.e. wet with) aqueous body liquids is away from the wearer (i.e., a wearer's waist is not substantially constricted by the caliper increase), the effective diameter of the wearer's waist is increased by the amount of caliper growth and by any lateral expansion that may occur. This causes the circumference of the absorbent article to effectively increase around the wearer's waist which results in additional stretching of the elastic elements. Mathematically, this growth can be stated as: Caliper growth by the bolstering waist feature 38 of an amount×mm averaged around the entire length of the band of tension results in stretching the elastic elements of the absorbent article by about an additional 2_×mm. For example, caliper growth of about 1 mm (~0.04 inches) results in stretching elastic elements about 6 mm (~0.25 inches). The resulting increase in contractive forces within the band of tension will depend on the specific stress/strain properties of the polymeric system used as an elastic member.

To insure that the bolstering waist feature 38 of the present invention compensates for a meaningful portion of the loss in contractive force due to stress relaxation, a bolstering waist feature of the present invention has a caliper growth ratio of at least greater than 3.0:1, preferably greater than 5.0:1, and most preferably greater than 7.0:1. As used herein, the term "caliper growth ratio" is intended to mean the ratio of the caliper of the bolstering waist feature 38 when it is fully saturated with synthetic aqueous body liquids (i.e., in its fully expanded state) to the caliper of the bolstering waist feature when it is in its dry state (i.e., in its fully contracted state). For example, in its most preferred embodiment the bolstering waist feature of the present invention has a dry caliper of about 1.5 mm and a wet caliper of 13.8 mm resulting in a caliper growth ratio of 9.2:1. Methods for measuring caliper in the fully expanded state (wet caliper) and in the fully contracted state (dry caliper) are given in the TEST METHODS section below.

The bolstering waist feature 38 of the present invention also compensates for reduced lateral tension in the waist region due to causes other than stress relaxation in elastic elements therein discussed above. Examples of other causes of reduced lateral tension in the waist region include stretching of non-elastic elements in the waist and slippage of the fastening system 36. In such cases, the effective circumference of the diaper 20 about the wearer's waist increases and the lateral tension in the waist regions decreases. By increasing in caliper as it becomes saturated with aqueous body liquids as is described above, the bolstering waist feature 28 of the present invention provides a force against the wearer's waist that results in a hoop stress in the waist region of the diaper 20 again tightening the diaper about the wearer's waist and compensating for the loss of lateral tension.

A bolstering waist feature 38 of the present invention must not only be able to grow in caliper as it becomes saturated with aqueous body liquids as discussed above, the bolstering waist feature 38 must be able to grow in caliper when subjected to in-use forces, such as the compressive forces within the band of tension. That is, the expansive force caused by the growth in caliper of the bolstering waist feature 38 must be greater than the compressive forces in the band of tension so that the bolstering waist feature 38 can compensate for stress relaxation. One measure of this ability to resist compressive forces is resistance to compression deflection. Resistance to compression deflection can be quantified for purposes of this invention by measuring the amount of strain (% caliper reduction) produced in a foam sample, which has been saturated and fully expanded with synthetic urine, after stress in the form of a 0.74 psi (5.1 kPa) confining pressure has been applied to the sample. Preferred embodiments of the bolstering waist feature 38 of the present invention have a resistance to compression deflection of less than about 40%. The method to measure resistance to compression deflection is discussed briefly in the TEST METHODS section below and more fully in the aforementioned U.S. Pat. No. 5,387,207.

While the physical properties of bolstering waist feature 38 discussed above can be provided by absorbent foam materials, such as the HIPE foams, that are preferred for at least a portion of the absorbent core 28 of the present invention, nothing said herein is intended to limit the present invention to only those materials. It is contemplated that bolstering waist features 38 of the present invention may comprise any materials or combinations of materials which possess either a caliper increase on wetting (i.e., a caliper growth ratio of at least 3.0:1), a dry cantilever bending value and wet cantilever bending value as described above (i.e., a cantilever bending ratio of at least 1.0:1), or both. For example, the bolstering waist feature 38 could comprise two elements one a stiffening element which provides a force resistive to bending and the other an element which provides compensation for stress relaxation in elastic elements of the absorbent article. Radiation crosslinked polyethylene foams sold by Voltek, Inc. of Lawrence, Mass. under the trade name Volara are suitable stiffening elements. Inflatable spacers, similar to those described in U.S. Pat. No. 5,330,459, issued to LaVon, et al. on Jul. 19, 1994, the disclosure of which is incorporated herein by reference, could provide the caliper increase on wetting to compensate for stress relaxation in elastic elements. For example, the inflatable spacers described therein preferably increase to a thickness of at least 10 times their uninflated thickness, more preferably at least 50 times their uninflated thickness (col. 6, lines 64–68). Embodiments with waist features that provide only stiffening or only a caliper increase are also contemplated.

The diaper 20 is preferably applied to a wearer by positioning one of the waist regions, preferably the second waist region 44, under the wearer's back and drawing the remainder of the diaper between the wearer's legs so that the other waist region, preferably the first waist region 42, is positioned across the front of the wearer. The tape tabs of the fastening system 36 are then released from the release portion of the fastening system. The diaperer then attaches one of the tape tabs to its corresponding landing zone and then grasps the remaining tape tab, pulls and attaches it to its landing zone. The elasticized side panels will typically be extended and tensioned during this operation so as to conform to the size and shape of the wearer.

In an alternative embodiment of the present invention, useful as a training pant or a pull on diaper, the portions of the longitudinal edges 54 of the diaper 20 that lie in waist regions 42 and 44 extend laterally outboard of the portion longitudinal edges 54 that lies in crotch region 46. That is, for this alternative embodiment, the diaper is wider in the waist regions 42 and 44 than in crotch region 46. Further, the longitudinal edges 54 in waist regions 42 and 44 are joined. That is, in this alternative embodiment of the present invention, the absorbent article is not provided with a fastening system. A band of lateral tension is still provided to the waist regions of this alternative embodiment of the present invention by elasticized portions, such as elasticized side panels. That is, the diaper 20 is folded about its transverse centerline 102 so that the first waist region 42 is opposite the second waist region 44. The opposed longitudinal edges 54 of the diaper 20 in the first and second waist regions (42 and 44 respectively) are then joined by means familiar to the art to form seams. Depending on the transverse width of the first waist region 42 relative to the second waist region 44, these seams may be positioned on the front, the side, or even in the rear of this alternative embodiment of the absorbent article as it is being worn. Examples of means of joining the edges to form seams are given in U.S. Pat. No. 5,236,430, issued to Bridges on Aug. 17, 1993, the disclosure of which is incorporated herein by reference.

TEST METHODS

In describing the present invention, a number of characteristics are set forth. Where reported, these characteristics can be determined using the following test fluids and test methods.

1) Test Fluid—Synthetic Urine

Several of the measurements described in the tests herein involve the use of a test fluid such as synthetic urine, ethanol, or 2-propanol (isopropyl alcohol). The synthetic urine utilized in a number of the tests described hereafter is made from a commercially available synthetic urine preparation manufactured by Jayco Pharmaceuticals (Mechanicsburg, Pa., 17055). This Jayco synthetic urine made from the preparation comprises KCl, 0.2%; $Na_2SO_4$, 0.2%; $NH_4H_2PO_4$, 0.085%; $(NH_4)_2HPO_4$, 0.015%; $CaCl_2*2H_2O$, 0.025%; and $MgCl_2*6H_2O$, 0.05%. (weight %'s) The synthetic urine samples are prepared according to the label instructions using distilled water. To aid dissolution, the Jayco salt mixture is slowly added to the water. The sample is filtered if necessary to remove any particulates. Any unused synthetic urine is discarded after one week. To improve visibility of the fluid, 5 drops of blue food color can be added per liter of synthetic urine solution. The Jayco synthetic urine utilized has a surface tension of 65±5 dynes/cm.

2) Free Absorbent Capacity

Free absorbent capacity can be quantified for purposes of this invention by measuring the amount synthetic urine absorbed by a sample of an absorbent material which has been saturated and expanded with synthetic urine.

The samples and Jayco synthetic urine are equilibrated to a temperature of 88° F. (31.1° C.). Measurements are performed at ambient temperature.

A sample sheet in its collapsed state is expanded and saturated to its free absorbent capacity by soaking in a bath of Jayco synthetic urine. After 3 minutes, a cylinder having a 1 in2 (6.5 cm2) circular surface area is cut out of the saturated, expanded sheet with a sharp circular die. The cylindrical sample is soaked in synthetic urine at 88° F. for a further 3 minutes. The sample is then removed from the synthetic urine solution and is placed on a digital balance. Any balance fitted with a weighing pan having an area larger than that of the sample and with a resolution of 1 milligram or less can be employed. Examples of such balances are the Mettler PM 480 and Mettler PC 440 (Mettler Instrument Corp.; Hightstown, N.J.).

After determining the weight of the wet sample (Ww), it is placed between 2 fine plastic mesh screens on top of 4 disposable paper towels. The sample is squeezed 3 times by firmly rolling a plastic roller over the top screen. The sample is then removed, soaked in distilled water for approximately 2 minutes, and squeezed between mesh screens as before. It is then placed between 8 layers of disposable paper towels (4 on each side) and pressed with 20,000 lbs. of force in a Carver Laboratory Press. The sample is then removed from the paper towels, dried in a Fisher convection oven at 180° F. for 20 minutes, and its dry weight recorded (Wd).

The free absorbent capacity is the wet weight (Ww) minus the dry weight (Wd) divided by the dry weight (Wd): ((Ww−Wd)/Wd)

The measurements for determining the free absorbent capacity of the sample may be made simultaneously with those for determining the resistance to compression deflection, and/or expansion factor.

3) Specific Surface Area per Foam Volume

Specific surface area per foam volume value is derived from (a) the capillary suction specific surface area that is measured during wetting of the dried foam structure, and (b) the density of the expanded foam structure after wetting to saturation, rather than by direct measurement of the dried, collapsed foam structure. See U.S. Pat. No. 5,387,207, issued to Dyer, et al. on Feb. 7, 1995, which is incorporated by reference, where specific area per foam volume is discussed in detail.

4) Capillary Absorption Pressures

A capillary absorption isotherm curve is generated using the Vertical Wicking Absorbent Capacity test described in the TEST METHODS section of U.S. Pat. No. 5,387,207, issued to Dyer, et al. on Feb. 7, 1995, which is incorporated by reference, except at 31° C. rather than 37° C. The curve is a plot of the absorbent capacity of each segment as a function of wicked height. The capillary absorption pressure is taken as the height of the foam that has an absorbent capacity one-half of the foam's free absorbent capacity.

5) Cantilever Bending Value

Cantilever bending value for the present invention is determined using ASTM Method D 1388 Standard Test Methods for Stiffness of Fabrics: Option A—Cantilever Test. The following modifications to this test method should be made:

1) Samples are conditioned to and testing conducted at 88° F., 55% relative humidity.
2) The test samples comprise sections of absorbent articles rather than of fabrics.
3) The flexural rigidity is measured only in the longitudinal direction since that is the direction of bending which results in loss of fit.
4) All samples are tested so they bent toward outer surface 64 since that is the direction of bending when a diaper folds over.
5) Samples are tested in both the dry state and when saturated.
6) Cantilever bending value equals the length of overhang as defined in ASTM method D 1388.

6) Stiffness Retention on Cyclical Flexing

Stiffness retention on flexing is determined from data generated using the cantilever bending value test described above. Specifically:

a) The initial cantilever bending value of the test sample is determined as described above.
b) The test sample is then cyclically flexed by orienting the sample so the long edges are aligned vertically, bending it to an angle of 70_relative to the vertical alingment in a first direction, returning it to an angle of 0_relative to the vertical alignment, and bending it to an angle of 70_relative to the vertical alingment in the opposite direction. A flexing cycle is defined as one bend to an angle of 70_in each direction and a return to 0_.
c) The flexing cycle is repeated 10 times at a rate of 10 flexing cycles per minute.
d) The cantilever bending value for the flexed sample is measured as described above.
e) A stiffness retention ratio for the sample may be calculated by dividing the cantilever bending value measured after the sample has been cyclically flexed by the initial cantilever bending value measured before flexure.

7) Wet and Dry Caliper

Caliper or thickness measurements for purposes of the present invention should be made when the sample is under a confining pressure of 0.05 psi (350 Pa).

A sample for caliper measurement is provided. A cylinder having a 1 in$^2$ (6.5 cm$^2$) circular surface area is punched out of the sample using a sharpened, circular die. A dial-type gauge suitable for making caliper measurements is positioned on the sample. Any gauge fitted with a foot having a circular surface area of at least 1 in$^2$ (6.5 cm$^2$) and capable of measuring caliper dimensions to 0.001 in (0.025 mm) can be employed. Examples of such gauges are an Ames model 482 (Ames Co.; Waltham, Mass.) or an Ono-Sokki model EG-225 (Ono-Sokki Co., Ltd.; Japan). Caliper measurements of three separate samples are taken.

Each sample is then saturated to its free absorbent capacity with Jayco synthetic urine. After 2 minutes, the caliper of each saturated, fully expanded sample is again measured.

8) Resistance to Compression Deflection

Resistance to compression deflection can be quantified for purposes of this invention by measuring the amount of strain (% caliper reduction) produced in a sample, which has been saturated and fully expanded with synthetic urine, after stress in the form of a 0.74 psi (5.1 kPa) confining pressure has been applied to the sample. In essence, the difference between caliper measured under a low confining pressure (0.05 psi (350 Pa)) and caliper measured at 0.74 psi (5.1 kPa) defines the strain caused by the higher confining pressure. This method is described more fully described in the TEST METHODS section of U.S. Pat. No. 5,387,207.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for fitting about a wearer's body, the absorbent article having longitudinal and lateral centerlines, which respectively define a longitudinal and a lateral direction, longitudinal edges, longitudinally opposed first and second waist regions, and a crotch region therebetween, the absorbent article comprising:

an outer cover;

an absorbent core joined to said outer cover, said absorbent core comprising at least a redistribution component which is capable of transporting aqueous body liquids from said crotch region to at least one of said waist regions;

means for creating lateral tension through at least a portion of said waist regions disposed in said waist regions; and a bolstering waist feature positioned in at least one of said waist regions, said bolstering waist feature being in effective fluid communication with said absorbent core, said bolstering waist feature having a caliper growth ratio of at least 3.0:1 such that said bolstering waist feature is at least able to counteract a portion of the loss of fit due to reduced lateral tension in said waist regions on wearing the absorbent article.

2. An absorbent article according to claim 1 wherein said outer cover comprises a liquid impervious backsheet and a liquid pervious topsheet joined with said backsheet; said absorbent core being positioned between said topsheet and said backsheet.

3. An absorbent article according to claim 2 wherein said bolstering waist feature has a caliper growth ratio of at least 5.0:1.

4. An absorbent article according to claim 2 wherein said bolstering waist feature has a caliper growth ratio of at least 7.0:1.

5. An absorbent article according to claim 2 wherein said bolstering waist feature is an extension of said redistribution component and comprises an absorbent polymeric foam.

6. An absorbent article according to claim 5 wherein said absorbent polymeric foam comprises a HIPE foam.

7. An absorbent article according to claim 2 wherein said bolstering waist feature is positioned in both said first and second waist regions.

8. An absorbent article for fitting about a wearer's body, the absorbent article having longitudinal and lateral centerlines, which respectively define a longitudinal and a lateral direction, longitudinal edges, longitudinally opposed first and second waist regions, and a crotch region therebetween, the absorbent article comprising:

an outer cover;

an absorbent core joined to said outer cover, said absorbent core comprising at least a redistribution component which is capable of transporting aqueous body liquids from said crotch region to said waist regions;

means for creating lateral tension through at least a portion of said waist regions disposed in said waist regions; and a bolstering waist feature positioned in least one of said waist regions, said bolstering waist feature being in effective fluid communication with said absorbent core, said bolstering waist feature having a cantilever bending ratio of at least 1.0:1.

9. An absorbent article according to claim 8 wherein said outer cover comprises a liquid impervious backsheet and a liquid pervious topsheet joined with said backsheet; said absorbent core being positioned between said topsheet and said backsheet.

10. An absorbent article according to claim 9 wherein said bolstering waist feature has a cantilever bending ratio of at least 1.1:1.

11. An absorbent article according to claim 9 wherein said bolstering waist feature has a cantilever bending ratio of at least 1.3:1.

12. An absorbent article for fitting about a wearer's body, the absorbent article having longitudinal and lateral centerlines, which respectively define a longitudinal and a lateral direction, longitudinal edges, longitudinally opposed first and second waist regions, and a crotch region therebetween, the absorbent article comprising:

an outer cover;

an absorbent core joined to said outer cover, said absorbent core comprising at least a redistribution component which is capable of transporting aqueous body liquids from said crotch region to said waist regions;

means for creating lateral tension through at least a portion of said waist regions disposed in said waist regions; and a bolstering waist feature positioned in least one of said waist regions, said bolstering waist feature being in effective fluid communication with said absorbent core, said bolstering waist feature having a stiffness retention ratio of at least 0.9:1 when dry.

13. An absorbent article according to claim 12 wherein said outer cover comprises a liquid impervious backsheet and a liquid pervious topsheet joined with said backsheet; said absorbent core being positioned between said topsheet and said backsheet.

14. An absorbent article according to claim 13 wherein said bolstering waist feature also has a stiffness retention ratio of at least 0.95:1 when dry.

15. An absorbent article for fitting about a wearer's body, the absorbent article having longitudinal and lateral centerlines, which respectively define a longitudinal and a lateral direction, longitudinally opposed first and second waist regions, and a crotch region therebetween, the absorbent article comprising:

a containment assembly having longitudinal sides and lateral ends which define the perimeter of said containment assembly, said containment assembly comprising a liquid pervious topsheet;

a liquid impervious backsheet joined with said topsheet;

an absorbent core positioned between said topsheet and said backsheet, said absorbent core comprising at least a fluid redistribution component;

a bolstering waist feature positioned in said first waist region, said bolstering waist feature being in effective fluid communication with said absorbent core, said bolstering waist feature having a caliper growth ratio of at least 5.0:1 and a cantilever bending ratio of at least 1.1:1;

at least one pair of laterally extending side panels positioned at least partially in one of said waist regions, wherein each of said side panels is joined to and extends laterally outward from one of said longitudinal sides of said containment assembly;

a fastening system, disposed on said first and second waist regions, for creating lateral tension through at least a portion of said waist regions.

16. An absorbent article according to claim 15 wherein said absorbent article further comprises a waistshield positioned between said bolstering waist feature and said topsheet, pairs of longitudinally extending side panels in both of said first and second waist regions, and longitudinally extending elasticized leg cuffs connectively associated with said longitudinal sides of said containment assembly.

17. An absorbent article according to claim 16 wherein said side panels in said second waist region are elasticized, said fastening system comprises a tape fastening means, and said elasticized leg cuffs comprise dual extended cuffs.

18. An absorbent article according to claim 17 wherein said bolstering waist feature has a caliper growth ratio of at least 7.0:1.

19. An absorbent article according to claim 16 wherein said containment assembly further comprises an elasticized waist feature extending longitudinally inward from said lateral end of said containment assembly that is in said second waist region toward said absorbent core, wherein said elasticized waist feature comprises at least a portion of said topsheet and said backsheet.

20. An absorbent article for fitting about a wearer's body, the absorbent article having longitudinal and lateral centerlines, which respectively define a longitudinal and a lateral direction, longitudinal sides and lateral ends, which define the periphery of the absorbent article, longitudinally opposed first and second waist regions, and a crotch region therebetween, the absorbent article comprising:

a liquid pervious topsheet;

a liquid impervious backsheet joined with said topsheet;

an absorbent core positioned between said topsheet and said backsheet, said absorbent core comprising at least a fluid redistribution component;

a fastening system, disposed on said first and second waist regions, for creating lateral tension through at least a portion of said waist regions; and a bolstering waist feature positioned in at least one of said waist regions, said bolstering waist feature being in effective fluid communication with said absorbent core, said bolstering waist feature having a caliper growth ratio of at least 5.0:1 and a cantilever bending ratio of at least 1.1:1.

21. An absorbent article according to claim 20 wherein said bolstering waist feature is an extension of said fluid redistribution component and comprises a HIPE foam.

22. An absorbent article according to claim 20 wherein said absorbent article further comprises laterally extending side panels in said first and second waist regions, a waist-shield positioned between said bolstering waist feature and said topsheet, and longitudinally extending elasticized leg cuffs connectively associated with said longitudinal sides of said absorbent article in at least said crotch region.

23. An absorbent article according to claim 22 wherein said side panels in said second waist region are elasticized.

24. An absorbent article according to claim 22 wherein said fastening system comprises a tape fastening means.

25. An absorbent article according to claim 22 wherein said fastening system comprises a mechanical fastening means.

26. An absorbent article according to claim 22 wherein said elasticized leg cuffs comprise dual extended cuffs.

27. An absorbent pant, the absorbent pant having longitudinal and lateral centerlines which respectively define a longitudinal and a lateral direction, longitudinal and lateral sides which define the periphery of the absorbent pant, longitudinally opposed first and second waist regions, and a crotch region therebetween, each of said waist regions having first and second longitudinal edges, the absorbent pant comprising:

an outer cover;

an absorbent core joined to said outer cover, said absorbent core comprising at least a fluid redistribution component which is capable of redistributing aqueous body liquids from said crotch region to said waist regions;

a bolstering waist feature positioned in at least one of said waist regions, said bolstering waist feature being in effective fluid communication with said absorbent core, said bolstering waist feature having a caliper growth ratio of at least 5.0:1 and a cantilever bending ratio of at least 1.1:1;

means, disposed on said first and second waist regions, for creating lateral tension through at least a portion of said waist regions; and seams joining said first longitudinal edge of said first waist region with said first longitudinal edge of said second waist region and said second longitudinal edge of said first waist region with said second longitudinal edge of said second waist region.

28. An absorbent article according to claim 27 wherein said outer cover comprises a liquid impervious backsheet and a liquid pervious topsheet joined with said backsheet, and said absorbent core is positioned between said topsheet and said backsheet, said absorbent core further comprising an acquisition component.

29. An absorbent article according to claim 28 wherein said means for creating lateral tension comprises elasticized side panels and said absorbent article further comprises longitudinally extending elasticized leg cuffs connectively associated with said longitudinal sides of said absorbent pant in at least said crotch region.

30. An absorbent article according to claim 27 wherein said bolstering waist feature extends longitudinally into both said first and second waist regions.

* * * * *